(12) United States Patent
Schröder et al.

(10) Patent No.: US 9,814,634 B2
(45) Date of Patent: Nov. 14, 2017

(54) FLUID-ABSORBENT ARTICLE

(71) Applicant: BASF SE, Ludwigshafen (DE)

(72) Inventors: Ulrich Schröder, Frankenthal (DE);
Rüdiger Funk, Niedernhausen (DE);
John Joseph Louden, Manchester (GB)

(73) Assignee: BASF SE, Ludwigshafen (DE)

( * ) Notice: Subject to any disclaimer, the term of this patent is extended or adjusted under 35 U.S.C. 154(b) by 736 days.

(21) Appl. No.: 13/649,559

(22) Filed: Oct. 11, 2012

(65) Prior Publication Data
US 2013/0096526 A1 Apr. 18, 2013

Related U.S. Application Data

(60) Provisional application No. 61/548,237, filed on Oct. 18, 2011.

(51) Int. Cl.
*A61F 13/15* (2006.01)
*A61F 13/537* (2006.01)
(Continued)

(52) U.S. Cl.
CPC .. *A61F 13/53708* (2013.01); *A61F 13/15747* (2013.01); *A61F 13/49001* (2013.01);
(Continued)

(58) Field of Classification Search
CPC .......... A61F 13/49001; A61F 13/55115; A61F 13/53747; A61F 13/5307; A61F 13/53765; A61F 2013/5307; A61F 2013/53765
(Continued)

(56) References Cited

U.S. PATENT DOCUMENTS 5,009,653 A * 4/1991 Osborn, III ....... A61F 13/15203
604/378
5,611,790 A * 3/1997 Osborn, III ........... A61F 13/472
604/373
(Continued)

FOREIGN PATENT DOCUMENTS

DE 196 01 664 A1 7/1997
JP 11216159 A 8/1999
(Continued)

OTHER PUBLICATIONS

International Search Report in international application No. PCT/EP2012/069447, dated May 31, 2013.
(Continued)

*Primary Examiner* — Jacqueline Stephens
(74) *Attorney, Agent, or Firm* — Marshall, Gerstein & Borun LLP

(57) ABSTRACT

The present invention relates to fluid-absorbent articles, comprising a fluid-absorbent core comprising at least 60% by weight of fluid-absorbent polymer particles and not more than 40% by weight of cellulose based fibers and an acquisition-distribution layer comprising at least 90% by weight of synthetic non-cellulose based fibers and not more than 10% by weight of cellulose based fibers. The thickness deviation of the bi-folded fluid-absorbent article in longitudinal direction is less than 10%. More particularly, the present invention relates to folding and packaging of disposable fluid-absorbent articles such as diapers, training pants.

14 Claims, 1 Drawing Sheet

(51) Int. Cl.
*A61F 13/49* (2006.01)
*A61F 13/551* (2006.01)
*A61F 13/532* (2006.01)
*A61F 13/53* (2006.01)

(52) U.S. Cl.
CPC ..... *A61F 13/5323* (2013.01); *A61F 13/53747* (2013.01); *A61F 13/55105* (2013.01); *A61F 13/55115* (2013.01); *A61F 2013/5307* (2013.01); *A61F 2013/530481* (2013.01); *A61F 2013/53765* (2013.01)

(58) Field of Classification Search
USPC .............. 604/385.201, 385.01, 385.101, 378
See application file for complete search history.

(56) References Cited

U.S. PATENT DOCUMENTS

| | | | |
|---|---|---|---|
| 6,050,984 A | | 4/2000 | Fujioka et al. |
| 6,702,798 B2 * | | 3/2004 | Christoffel et al. ... 604/385.201 |
| 2004/0167489 A1 | | 8/2004 | Kellenberger et al. |
| 2007/0250028 A1 * | | 10/2007 | Woltman ............ A61F 13/4704 604/385.02 |
| 2007/0264115 A1 | | 11/2007 | Orth |
| 2008/0082075 A1 * | | 4/2008 | Morrell-Schwartz .. 604/385.201 |

FOREIGN PATENT DOCUMENTS

| | | |
|---|---|---|
| JP | 2000042028 A | 2/2000 |
| WO | WO-2004/073571 A1 | 9/2004 |
| WO | WO-2005/097636 A1 | 10/2005 |
| WO | WO-2010/062233 A1 | 6/2010 |
| WO | WO-2011/087503 A1 | 7/2011 |

OTHER PUBLICATIONS

U.S. Appl. No. 13/031,468, filed Feb. 21, 2011.
U.S. Appl. No. 13/032,410, filed Feb. 22, 2011.
U.S. Appl. No. 13/071,041, filed Mar. 24, 2011.
U.S. Appl. No. 13/208,690, filed Aug. 12, 2011.
U.S. Appl. No. 13/232,767, filed Sep. 14, 2011.
U.S. Appl. No. 13/463,545, filed May 3, 2012.
U.S. Appl. No. 13/478,423, filed May 23, 2012.
U.S. Appl. No. 13/484,849, filed May 31, 2012.
U.S. Appl. No. 13/487,829, filed Jun. 4, 2012.

* cited by examiner

FLUID-ABSORBENT ARTICLE

CROSS-REFERENCE TO RELATED APPLICATIONS

This application claims the benefit of U.S. provisional patent application No. 61/548,237, filed Oct. 18, 2011, incorporated herein by reference in its entirety.

The present invention relates to fluid-absorbent articles, comprising a fluid-absorbent core comprising at least 60% by weight of fluid-absorbent polymer particles and not more than 40% by weight of cellulose based fibers and an acquisition-distribution layer comprising at least 90% by weight of synthetic non-cellulose based fibers and not more than 10% by weight of cellulose based fibers. The thickness deviation of the bi-folded fluid-absorbent article in longitudinal direction is less than 10%. More particularly, the present invention relates to folding and packaging of disposable fluid-absorbent articles such as diapers, training pants.

The production of fluid-absorbent articles such as fluid-absorbent articles is described in the monograph "Modern Superabsorbent Polymer Technology", F. L. Buchholz and A. T. Graham, Wiley-VCH, 1998, pages 252 to 258.

Fluid-absorbent articles consist typically of an upper liquid-pervious top-sheet, a lower liquid-impervious layer, an absorption and distribution layer and fluid-absorbing composite between the top-sheet and the liquid-impervious layer. The composite consists of fluid-absorbing polymers and fibers. Further layers are, for example tissue layers.

The preparation of fluid-absorbing polymer particles is likewise described in the monograph "Modern Superabsorbent Polymer Technology", F. L. Buchholz and A. T. Graham, Wiley-VCH, 1998, pages 71 to 103. The fluid-absorbing polymer particles are also referred to as superabsorbents.

Fluid-absorbent articles are commercially packaged in packages which include multiple articles therein. Prior to packaging, fluid-absorbent articles, such as diapers, are usually folded such that each longitudinal side is folded inward toward the crotch region and then the diaper is folded at the center so that it overlaps itself to form a rectangular shape. As the acquisition-distribution layer normally is positioned asymmetrically on the upper part of the absorbent core, bi-folding results in an article of rectangular shape, but inequality/inhomogeneity in respect to their thickness. The part of the folded articles comprising the crotch region is much thicker than e.g. the opposite side of the folded article. Furthermore the individual articles in total are relatively thick and consume considerable space for example due to the high amount of chemical modified cellulose based fibers.

To save space in packaging the fluid-absorbent articles are bundled and then compressed to reduce the bundle volume. Despite of this compression and therefore generally reduction in volume the fluid-absorbent articles are still uneven because of the differences in thickness described above.

These differences in thickness also prohibit or make it very difficult to use the space in the packages to full extent, packages may contain a certain amount of dead space. As the price e.g. for a diaper results to a high percentage also from transport costs, the dead space results in higher costs for the fluid-absorbent articles.

Furthermore compression-packed articles are held in place by a strong, but flexible polymer material, such as polyethylene. As the articles in the compressed state tend to return to their original thickness, there will be a relatively high pressure against the walls of the package. As folding is effected in the crotch part of the article, which is the most sensitive part of the fluid-absorbent article, high compressive forces facilitate pin-holing of the lower layers of a diaper.

In addition conventional fibers used, such as cellulose fibers tend to stay in the pressed conformation even after reducing the pressure. They are not able to retrieve their conformation/structure after compression takes place. This leads to a loss of performance of the fluid-absorbing article due to packaging.

To overcome this problem several attempts were made, e.g. the folding of fluid-absorbent articles has been improved or special packaging technologies have been developed.

For example JP 3 411 205 B2 discloses to improve packaging a folding method. The diaper is folded two times along the longitudinal direction, and then bi-fold to get a rectangular shape. This folded diaper is easily expanded from packaging.

WO 2004 073571 A1 discloses a disposable absorbent article having a special folded configuration much smaller and more compact compared to its unfolded use configuration. A ratio between the folded configuration and the unfolded configuration is less than 0.09. The article is positioned and sealed in a vacuum package.

WO 2010062233 A1 deals with a method of package folding for a disposable sanitary article having a belt so that the folded article attains a rectangular shape and a desired size.

According to JP 3 841 562 B2 the fluid-absorbent articles are folded to a peculiar shape and arranged in parallel in the package to ensure a compact packaging of the articles. This process furthermore is suitable to be carried out by machines, whereas the stacking of the folded fluid-absorbent articles is the fastest in the case of parallel packaging.

In DE 19601664 A1 a special process for packaging fluid-absorbent articles is described wherein the articles are alternately oriented. The same method of stacking is disclosed in WO 2005 097636 by using a rotating chain.

No efforts were made to optimize the fluid-absorbent articles.

It was therefore an object of the present invention to provide fluid-absorbent articles with improved configurations to assure using the space in the packages to almost full capacity, avoiding dead space.

Furthermore it is an object of the present invention to provide fluid-absorbent articles with improved composition assuring that the fluid-absorbent article is not damaged by compression packaging and retain its full performance when the pressure is reduced.

The object is achieved by a bi-folded fluid-absorbent absorbent article comprising (A) an upper liquid-pervious layer,
(B) a lower liquid-impervious layer,
(C) a fluid-absorbent core between (A) and (B) comprising at least 60% by weight of fluid-absorbent polymer particles and not more than 40% by weight of cellulose based fibers, based on the sum of fluid-absorbent polymer particles and cellulose based fibers, and
(D) an acquisition-distribution layer between (A) and (C) comprising at least 90% by weight of synthetic non-cellulose based fibers and not more than 10% by weight of cellulose based fibers, based on the sum of synthetic non-cellulose based fibers and cellulose based fibers, wherein the acquisition-distribution layer (D) is in longitudinal direction asymmetric positioned on the fluid-absorbent core (C), the thickness of the acquisition-distribution layer (D) is not more than 60% of the thickness of the fluid-absorbent core (C) and the thickness deviation of the bi-folded fluid-absorbent article in longitudinal direction is less than 10%.

The acquisition distribution layer (D), comprising at least 90% by weight of synthetic non-cellulose based fibers and not more than 10% by weight of cellulose based fibers, preferable at least 95%, more preferred 98% most preferred 100% by weight of synthetic non-cellulose based fibers and preferable not more than 5%, more preferred not more than 2% and most preferred the acquisition distribution layer (D) is essentially free of cellulose based fibers.

The acquisition distribution layer (D) preferably comprises a high loft synthetic non-cellulose based fibers carded web, which may be bonded by air, heat, calendaring and/or modifications such as resin additives and/or chemical binders or combinations thereof.

Multiple fiber types and/or blends thereof are suitable, for example polyester, co-polyester, polypropylene, polyethylene, polylactic acid or polyamide. Furthermore the linear mass density of fibers (decitex, abbreviated dtex, which is the mass in grams per 10,000 meters) may be optimised for use in acquisition distribution layer (ADL). For example 6-7 dtex for polyester and copolyester for an ADL of 40-60 gsm. Another example of ADL for light incontinence fluid-absorbent articles comprises polypropylene fibers of 3.3 dtex and polyethylene fibers of 3.2 dtex. Bi- or multi-component fibres comprising differing thermal responses can be used. They may improve functionality of the ADL (D) and/or 'soft feel' for the user of the hygienic article.

The synthetic non-cellulose based fibers suitable for use in acquisition distribution layer (D) have a strength suitable to be compressed e.g. in brick package, usually used for diapers, and able to return into the original conformation without fiber breakage or deformation caused by the pressure necessary for packaging.

Furthermore the acquisition distribution layer (D) of the fluid absorbent-article according to the present invention is preferably not more than 55% of the thickness of the fluid-absorbent core, more preferred not more than 53% and most preferred not more than 50% of the thickness of the fluid-absorbent core.

The fluid absorbent core (C) of the fluid absorbent-article comprises typically at least 60%, preferably at least 70%, more preferred at least 80% and most preferred at least 90% by weight of fluid-absorbent polymer particles.

The fluid absorbent core (C) of the fluid absorbent article may contain different amounts of fluid-absorbent polymer particles depending on targeted use. For example a maxi size/L/04 diaper contains at least 8 g, more preferably at least 11 g, most preferably at least 13 g of the fluid-absorbent polymer particles.

Fluid-absorbent polymer particles suitable for the inventive fluid-absorbing articles have an apparent bulk density of preferably 0.47 to 0.78 g/cm$^3$, more preferably 0.55 to 0.75 g/cm$^3$, most preferably 0.60 to 0.70 g/cm$^3$.

Suitable fluid-absorbent polymer particles for the inventive fluid-absorbent articles have a saline flow conductivity (SFC) of at least $8 \times 10^{-7}$ cm$^3$ s/g, typically at least $20 \times 10^{-7}$ cm$^3$ s/g, preferably at least $25 \times 10^{-7}$ cm$^3$ s/g, preferentially preferably at least $30 \times 10^{-7}$ cm$^3$ s/g, most preferably at least $50 \times 10^{-7}$ cm$^3$ s/g. The saline flow conductivity (SFC) of the fluid-absorbent polymer particles is typically less than $500 \times 10^{-7}$ cm$^3$ s/g.

Suitable fluid-absorbent polymer particles for the fluid-absorbent articles according to the invention have a centrifuge retention capacity (CRC) preferably of at least 20 g/g, most preferably of at least 24 g/g. The centrifuge retention capacity (CRC) of the fluid-absorbent polymer particles is typically less than 60 g/g.

Suitable fluid-absorbent polymer particles for the inventive fluid-absorbent articles have a absorbency under high load of typically at least 18 g/g, preferably at least 20 g/g, more preferably at least 22 g/g, most preferably at least 24 g/g. The absorbency under high load of the fluid-absorbent polymer particles is typically less than 35 g/g.

Suitable fluid-absorbent polymer particles for the inventive fluid-absorbent articles are described in e.g. EP 1 770 113, WO 04/113452, WO 00/053644, WO 00/053664, WO 02/20068, WO 02/22717, WO 06/42704, WO 08/9580.

In one embodiment the fluid-absorbent polymer particles are placed in discrete regions of the fluid-absorbent core.

The fluid-absorbent core (C) furthermore comprises preferably not more than 30%, more preferred not more than 20% and most preferred not more than 10% by weight, of cellulose based fibers, based on the sum of fluid-absorbent polymer particles and cellulose based fibers.

In case the fluid-absorbing articles are diapers the length of the acquisition-distribution layer in its longitudinal direction typically is at least 55%, preferred at least 60%, more preferred at least 62.5% of the length of the fluid-absorbent core.

In a further embodiment the distance between the centers of the fluid-absorbent core and the acquisition-distribution layer is typically from 5 to 20%, preferably from 8 to 18%, more preferably from 12 to 17% most preferred 14 to 16% of the total length of the fluid-absorbent core.

In yet another preferred embodiment of the present invention, the thickness of the unfolded fluid-absorbent article is less than 3 mm, more preferred less than 2.5 mm.

The fluid-absorbing article according the present invention has in the bi-folded conformation an almost rectangular shape, with an extension in longitudinal direction greater than in lateral direction. The bi-folded fluid-absorbing articles show a thickness deviation in longitudinal direction of typically less than 10%, preferred less than 8%, more preferred of less than 5% and most preferred of less than 4%. These fluid-absorbing articles, especially diapers, may be easily packed using conventional packing technology. Even without the usual pressure compression packaging the packages may not contain a significant amount of dead space.

Furthermore the manufacturing of the fluid-absorbent articles does not require any special inventive technology, state of the art technology is sufficient.

Thus, the fluid-absorbent articles according to the present invention have reduced costs and are less expensive because of similar manufacturing as conventional articles and higher economic impact because of more effective logistics, especially in transport and storage notwithstanding reduced consumer packaging costs and increased diaper packages per square sales meter at point of sale.

Due to a more homogeneous compression the risk of pin-holing in the packaging step is reduced.

DETAILED DESCRIPTION OF THE INVENTION

A. Definitions

As used herein, the term "fluid-absorbent article" refers to any three-dimensional solid material being able to acquire and store fluids discharged from the body. Preferred fluid-absorbent articles are disposable fluid-absorbent articles that are designed to be worn in contact with the body of a user such as disposable fluid-absorbent pantyliners, sanitary napkins, catamenials, incontinence inserts/pads, diapers, training pant diapers, breast pads, interlabial inserts/pads or other articles useful for absorbing body fluids.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" refers to a fluid-absorbent composition comprising fluid-absorbent polymer particles and a fibrous material. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein the term "x-dimension" refers to the length, and the term "y-dimension" refers to the width of the fluid-absorbent composition, layer, core or article. Generally, the term "x-y-dimension" refers to the plane, orthogonal to the height or thickness of the fluid-absorbent composition, layer, core or article.

As used herein the term "z-dimension" refers to the dimension orthogonal to the length and width of the fluid absorbent composition, layer, core or article. Generally, the term "z-dimension" refers to the height of the fluid-absorbent composition, layer, core or article.

As used herein, the term "density" indicates the weight of the fluid-absorbent core per volume and it includes the chassis of the fluid-absorbent article. The density is determined at discrete regions of the fluid-absorbent core: the front overall average is the density of the fluid-absorbent core 5.5 cm forward of the center of the core to the front distal edge of the core; the insult zone is the density of the fluid-absorbent core 5.5 cm forward and 0.5 cm backwards of the center of the core; the back overall average is the density of the fluid-absorbent core 0.5 cm backward of the center of the core to the rear distal edge of the core.

Further, it should be understood, that the term "upper" refers to fluid-absorbent composition which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the component which is furthermost away from the wearer of the fluid-absorbent article, hereinafter described as "lower liquid-impervious layer".

As used herein, the term "liquid-pervious" refers to a substrate, layer or a laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

As used herein, the term "chassis" refers to fluid-absorbent material comprising the upper liquid-pervious layer and the lower liquid-impervious layer, elastication and closure systems for the absorbent article.

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, term "hydrophobic" refers to fibers showing a contact angle of greater than 90° or no spontaneously spreading of the liquid across the surface of the fiber.

As used herein, the term "body fluids" refers to any fluid produced and discharged by human or animal body, such as urine, menstrual fluids, faeces, vaginal secretions and the like.

As used herein, the term "breathable" refers to a substrate, layer, film or a laminate that allows vapour to escape from the fluid-absorbent article, while still preventing fluids from leakage. Breathable substrates, layers, films or laminates may be porous polymeric films, nonwoven laminates from spunbond and melt-blown layers, laminates from porous polymeric films and nonwovens.

As used herein, the term "longitudinal" refers to a direction running perpendicular from a waist edge to an opposing waist edge of the fluid-absorbent article.

B. Fluid-Absorbent Polymer Particles

The production of fluid-absorbing polymer particles is described in the monograph "Modern Superabsorbent Polymer Technology", F. L. Buchholz and A. T. Graham, Wiley-VCH, 1998, pages 71 to 103.

The fluid-absorbing polymer particles are produced, for example, by polymerizing a monomer solution or suspension comprising
 a) at least one ethylenically unsaturated monomer which bears acid groups and may be at least partly neutralized,
 b) at least one crosslinker,
 c) at least one initiator,
 d) optionally one or more ethylenically unsaturated monomers copolymerizable with the monomers mentioned under a) and
 e) optionally one or more water-soluble polymers,
 and are typically water-insoluble.

The fluid-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a).

Useful purification methods are disclosed in WO 2002/055469 A1, WO 2003/078378 A1 and WO 2004/035514 A1.

A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used for the inventive process.

The content of acrylic acid and/or salts thereof in the total amount of monomers a) is preferably at least 50 mol %, more preferably at least 90 mol %, most preferably at least 95 mol %.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tatrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for cross-linking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

The initiators are used in customary amounts, for example in amounts of from 0.001 to 5% by weight, preferably from 0.01 to 2% by weight, based on the monomers a).

Particularly preferred initiators c) are azo initiators such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

Useful water-soluble polymers e) include polyvinyl alcohol, polyvinylpyrrolidone, starch, starch derivatives, modified cellulose, such as methylcellulose or hydroxyethylcellulose, gelatin, polyglycols or polyacrylic acids, polyesters and polyamides, polylactic acid, polyvinylamine, preferably starch, starch derivatives and modified cellulose.

The water content of the monomer solution is preferably less than 65% by weight, preferentially less than 62% by weight, more preferably less than 60% by weight, most preferably less than 58% by weight.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 85 mol %, for "acidic" polymer gels more preferably from 30 to 60 mol %, most preferably from 35 to 55 mol %, and for "neutral" polymer gels more preferably from 65 to 80 mol %, most preferably from 70 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts, such as the salt of triethanolamine. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA recommended test method No. WSP 230.3-10 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 µm, more preferably from 250 to 600 µm, very particularly from 300 to 500 µm. The mean particle size of the product fraction may be determined by means of EDANA recommended test method No. WSP 220.3-10 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 100 µm is preferably at least 90% by weight, more preferably at least 95% by weight, most preferably at least 98% by weight.

Polymer particles with too small particle size lower the saline flow conductivity (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 µm is preferably at least 90% by weight, more preferably at least 95% by weight, most preferably at least 99% by weight.

Excessively large polymer particles are typically removed and recycled into the grinding of the dried polymer gel.

To further improve the properties, the polymer particles can be surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1,2-oxazolidone and its derivatives, such as 2-hydroxyethyl-2-oxazolidone in DE 198 07 502 A1, bis- and poly-2-oxazolidinones in DE 198 07 992 C1,2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment, polyvalent cations are applied to the particle surface in addition to the surface postcrosslinkers before, during or after the surface postcrosslinking.

The polyvalent cations usable are, for example, divalent cations such as the cations of zinc, magnesium, calcium and strontium, trivalent cations such as the cations of aluminum, tetravalent cations such as the cations of titanium and zirconium. Possible counterions are, for example, chloride, bromide, sulfate, hydrogensulfate, carbonate, hydrogencarbonate, nitrate, phosphate, hydrogenphosphate, dihydrogenphosphate and carboxylate, such as acetate and lactate. Aluminum sulfate and aluminum lactate are preferred. Apart from metal salts, it is also possible to use polyamines as polyvalent cations. A single metal salt can be used as well as any mixture of the metal salts and/or the polyamines above.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spraying of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact dryers, more preferably paddle dryers, most preferably disk dryers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of using polyfunctional epoxides, Holo-Flite® dryers are preferred. Moreover, it is also possible to use fluidized bed dryers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed dryer.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

It is preferable to cool the polymer particles after thermal drying. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures of in the range from 20 to 150° C., preferably from 40 to 120° C., more preferably from 60 to 100° C., most preferably from 70 to 90° C. Cooling using warm water is preferred, especially when contact coolers are used.

Subsequently, the surface postcrosslinked polymer particles can be classified again, excessively small and/or excessively large polymer particles being removed and recycled into the process.

To further improve the properties, the surface postcrosslinked polymer particles can be coated and/or remoisturized.

Suitable coatings for controlling the acquisition behavior and improving the permeability (SFC or GBP) are, for example, inorganic inert substances, such as water-insoluble metal salts, organic polymers, cationic polymers and polyvalent metal cations. Suitable coatings for improving the color stability are, for example reducing agents and antioxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium monoacetate, aluminium sulfate, aluminium lactate, Brüggolite® FF7 and Span® 20.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the fluid-absorbent polymer particles are coated with inorganic inert substances, the amount of inorganic inert substances used, based on the fluid-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene, polypropylene, polyamides or polytetrafluoro-ethylene. Other examples are styrene-isoprene-styrene block-copolymers or styrene-butadiene-styrene block-copolymers.

Suitable cationic polymers are polyalkylenepolyamines, cationic derivatives of polyacrylamides, polyethyleneimines and polyquaternary amines.

Polyquaternary amines are, for example, condensation products of hexamethylenedi-amine, dimethylamine and epichlorohydrin, condensation products of dimethylamine and epichlorohydrin, copolymers of hydroxyethylcellulose and diallyldimethylammo-nium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, poly-functional acids or poly-functional (meth)acrylates.

It is possible to use all polyfunctional amines having primary or secondary amino groups, such as polyethyleneimine, polyallylamine and polylysine. The liquid sprayed by the process according to the invention preferably comprises at least one polyamine, for example polyvinylamine or a partially hydrolyzed polyvinylformamide.

The cationic polymers may be used as a solution in an aqueous or water-miscible solvent, as dispersion in an aqueous or water-miscible dispersant or in substance.

When the fluid-absorbent polymer particles are coated with a cationic polymer, the use amount of cationic polymer based on the fluid-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride, hydroxide, carbonate, nitrate and sulfate. The metal salts are preferably used as a solution or as a stable aqueous colloidal dispersion. The solvents used for the metal salts may be water, alcohols, dimethylfor-mamide, dimethyl sulfoxide and mixtures thereof. Particular preference is given to water and water/alcohol mixtures, such as water/methanol, water/isopropanol, water/1,3-propanediole, water/1,2-propandiole/1,4-butanediole or water/propylene glycol.

When the fluid-absorbent polymer particles are coated with a polyvalent metal cation, the amount of polyvalent metal cation used, based on the fluid-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophos-phite, salts of sulfinic acids, for example the disodium salt of 2-hydroxy-2-sulfinato-acetic acid, and addition products of aldehydes, for example the disodium salt of 2-hy-droxy-2-sulfonatoacetic acid. The reducing agent used can be, however, a mixture of the sodium salt of 2-hydroxy-2-sulfinatoacetic acid, the disodium salt of 2-hydroxy-2- sulfonatoacetic acid and sodium bisulfite. Such mixtures are obtainable as Brüggolite® FF6 and Brüggolite® FF7 (Brüggemann Chemicals; Heilbronn; Germany).

The reducing agents are typically used in the form of a solution in a suitable solvent, preferably water. The reducing agent may be used as a pure substance or any mixture of the above reducing agents may be used.

When the fluid-absorbent polymer particles are coated with a reducing agent, the amount of reducing agent used, based on the fluid-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the fluid-absorbent polymer particles only insignificantly. The polyols are preferably used as a solution in aqueous or water-miscible solvents.

When the fluid-absorbent polymer particles are coated with a polyol, the use amount of polyol, based on the fluid-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

The fluid-absorbing polymer particles have a centrifuge retention capacity (CRC) of at least 15 g/g, typically at least 20 g/g, preferably at least 24 g/g, preferentially at least 26 g/g, more preferably at least 28 g/g, most preferably at least 30 g/g. The centrifuge retention capacity (CRC) of the fluid-absorbing polymer particles is typically less than 60 g/g. The centrifuge retention capacity (CRC) is determined by EDANA recommended test method No. WSP 241.3-10 "Centrifuge Retention Capacity".

The fluid-absorbing polymer particles have an absorbency under a load of 49.2 g/cm$^2$ of typically at least 18 g/g, preferably at least 20 g/g, more preferably at least 22 g/g, most preferably at least 24 g/g. The absorbency under a load of 49.2 g/cm$^2$ of the fluid-absorbing polymer particles is typically less than 35 g/g. The absorbency under a load of 49.2 g/cm$^2$ is determined analogously to EDANA recommended test method No. WSP 242.3-10 "Absorption under Pressure".

The fluid-absorbent polymer particles have a saline flow conductivity (SFC) of at least $8\times10^{-7}$ cm$^3$ s/g, typically at least $20\times10^{-7}$ cm$^3$ s/g, preferably at least $25\times10^{-7}$ cm$^3$ s/g, preferentially preferably at least $30\times10^{-7}$ cm$^3$ s/g, most preferably at least $50\times10^{-7}$ cm$^3$ s/g. The saline flow conductivity (SFC) of the fluid-absorbent polymer particles is typically less than $500\times10^{-7}$ cm$^3$ s/g. The saline flow conductivity is basically determined according to EP 0 640 330 A1, as the gel layer permeability of a swollen gel layer of fluid-absorbent polymer particles.

C. Fluid-Absorbent Articles

The fluid-absorbent article comprises of
(A) an upper liquid-pervious layer,
(B) a lower liquid-impervious layer,
(C) a fluid-absorbent core between (A) and (B) comprising
  At least 60% by weight fluid-absorbent polymer particles and not more than 40% by weight of cellulose based fibers,
  preferably at least 70% by weight fluid-absorbent polymer particles and not more than 30% by weight of cellulose based fibers,
  more preferably at least 80% by weight fluid-absorbent polymer particles and not more than 20% by weight of cellulose based fibers,
  most preferably at least 90% by weight fluid-absorbent polymer particles and not more than 10% by weight of cellulose based fibers, based on the sum of fluid-absorbent polymer particles and cellulose based fibres, and
(D) an acquisition-distribution layer between (A) and (C) comprising at least 90% by weight of synthetic non-cellulose based fibers and not more than 10% by weight of cellulose based fibers,
  preferably at least 95% by weight of synthetic non-cellulose based fibers and not more than 5% by weight of cellulose based fibers,
  more preferably at least 98% by weight of synthetic non-cellulose based fibers and not more than 2% by weight of cellulose based fibers,
  most preferably at least 100% by weight of synthetic non-cellulose based fibers and essential free of cellulose based fibers,
  based on the sum of synthetic non-cellulose based fibres and acquisition-distribution layer,
  wherein the acquisition-distribution layer (D) is in longitudinal direction asymmetric positioned on the fluid-absorbent core (C).

The thickness of the acquisition-distribution layer (D) is not more than 60%, preferably not more than 55%, more preferred not more than 53% and most preferred not more than 50% of the thickness of the fluid-absorbent core (C).

The thickness deviation of the bi-folded fluid-absorbent article in longitudinal direction is less than 10%, preferably less than 8%, most preferred of less than 5% and most of all preferred of less than 4%.

Fluid-absorbent articles are understood to mean, for example, incontinence pads and incontinence briefs for adults or diapers for babies. Suitable fluid-absorbent articles including fluid-absorbent compositions comprising fibrous material and optionally fluid-absorbent polymer particles to form fibrous webs or matrices for the substrates, layers, sheets and/or the fluid-absorbent core.

Suitable fluid-absorbent articles are composed of several layers whose individual elements must show preferably definite functional parameters such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapour breathability, dryness, wearing comfort and protection on the one side, and concerning liquid retention, rewet and prevention of wetting through on the other side. The specific combination of these layers provides a fluid-absorbent article delivering both high protection levels as well as high comfort to the consumer.

I. Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic non-cellulose based or semisynthetic fibers or bicomponent fibers or films of polyester, polyolefins, rayon or natural cellulose based fibers or any combinations thereof. In the case of nonwoven materials, the fibers should generally be bound by binders such as polyacrylates. Additionally the liquid-pervious layer may contain elastic compositions thus showing elastic characteristics allowing to be stretched in one or two directions.

Suitable synthetic non-cellulose based fibers are made from polyvinyl chloride, polyvinyl fluoride, polytetrafluoroethylene, polyvinylidene chloride, polyacrylics, polyvinylacetate, polyethylvinylacetate, non-soluble or soluble polyvinyl alcohol, polylactic acid, polyolefins such as polyethylene, polypropylene, polyamides, polyesters, polyurethanes, polystyrenes and the like.

A detailed overview of examples of fibers which can be used in the present invention is given by the patent application WO 95/26209 A1, page 28 line 9 to page 36 line 8. Said passage is thus part of this invention.

Examples of cellulose fibers include cellulose fibers which are customarily used in absorption products, such as fluff pulp and cellulose of the cotton type. The materials (soft- or hardwoods), production processes such as chemical pulp, semichemical pulp, chemothermomechanical pulp (CTMP) and bleaching processes are not particularly restricted. For example, natural cellulose fibers such as cotton, flax, silk, wool, jute, ethylcellulose and cellulose acetate are used.

Suitable synthetic fibers are produced from polyvinyl chloride, polyvinyl fluoride, polytetrafluoroethylene, polyvinylidene chloride, polyacrylic compounds such as ORLON®, polyvinyl acetate, polyethyl vinyl acetate, soluble or insoluble polyvinyl alcohol. Examples of synthetic fibers include thermoplastic polyolefin fibers, such as polyethylene fibers (PULPEX®), polypropylene fibers and polyethylene-polypropylene bicomponent fibers, polyester fibers, such as polyethylene terephthalate fibers (DACRON® or KODEL®), copolyesters, polyvinyl acetate, polyethyl vinyl acetate, polyvinyl chloride, polyvinylidene chloride, polyacrylics, polyamides, copolyamides, polystyrene and copolymers of the aforementioned polymers and also bicomponent fibers composed of polyethylene terephthalate-polyethylene-isophthalate copolymer, polyethyl vinyl acetate/polypropylene, polyethylene/polyester, polypropylene/polyester, copolyester/polyester, polyamide fibers (nylon), polyurethane fibers, polystyrene fibers and polyacrylonitrile fibers. Preference is given to polyolefin fibers, polyester fibers and their bicomponent fibers. Preference is further given to thermally adhesive bicomponent fibers composed of polyolefin of the core-sheath type and side-by-side type on account of their excellent dimensional stability following fluid absorption.

The fiber cross section may be round or angular, or else have another shape, for example like that of a butterfly.

The synthetic fibers mentioned are preferably used in combination with thermoplastic fibers. In the course of the heat treatment, the latter migrate to some extent into the matrix of the fiber material present and so constitute bond sites and renewed stiffening elements on cooling. In addition, the addition of thermoplastic fibers means that there is an increase in the present pore dimensions after the heat treatment has taken place. This makes it possible, by continuous metered addition of thermoplastic fibers during the formation of the absorbent layer, to continuously increase the fraction of thermoplastic fibers in the direction of the topsheet, which results in a similarly continuous increase in the pore sizes. Thermoplastic fibers can be formed from a multitude of thermoplastic polymers which have a melting point of less than 190° C., preferably in the range from 75° C. to 175° C. These temperatures are too low for damage to the cellulose fibers to be likely.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural cellulose based fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural cellulose based fibers or synthetic non-cellulose based fibers or any combination thereof. Preferred materials are polyester, rayon and blends thereof, polyethylene, and polypropylene.

The fibrous material as a component of the fluid-absorbent article may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of fluid-absorbent polymer particles of the resulting fluid-absorbent article. Such, the use of hydrophobic fibers is preferred if the fluid-absorbent article is adjacent to the wearer, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulose based fibers, modified cellulose based fibers, rayon, polyester fibers such as polyethylene terephthalate, hydrophilic nylon and the like. Hydrophilic fibers can also be obtained from hydrophobic fibers which are hydrophilized by e.g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of rising the temperature in the presence of low-melting polymers. Examples for thermal bonding processes are spun-bonding, through-air bonding and resin bonding.

Preferred means of increasing the integrity are thermal bonding, spun-bonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulose based fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a mono-compo-nent fiber. Alternatively, they can be made from more than one polymer, e.g., bi-component or multi-component fibers. The term "bi-component fibers" refers to thermoplastic fibers that comprise a core fiber made from a different fiber material than the shell. Typically, both fiber materials have different melting points, wherein generally the sheath melts at lower temperatures. Bi-component fibers can be helical, concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent article is the spun-bonding technology. The nature of the production of fibrous layers by means of spunbonding is based on the direct spinning of polymeric granulates into continuous filaments and subsequently manufacturing the fibrous layer.

Spun-bond fabrics are produced by depositing extruded, spun fibers onto a moving belt in a uniform random manner followed by thermal bonding the fibers. The fibers are separated during the web laying process by air jets. Fibre bonds are generated by applying heated rolls or hot needles to partially melt the polymer and fuse the fibers together. Since molecular orientation increases the melting point, fibers that are not highly drawn can be used as thermal binding fibres. Polyethylene or random ethylene/-propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermally treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 Bar are used to direct the water jets onto the web. This pressure is sufficient for most of the non-woven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behaviour of the layer. If there is further some profiled structure integrated, the acquisition-distribution behavior can be directed depending on the three-dimensional structure of the layer. Thus 3D-polyethylene in the function of liquid-pervious layer is preferred.

Thus, suitable liquid-pervious layers (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious layers (A) extend partially or wholly across the fluid-absorbent structure and can extend into and/or form part of all the preferred sideflaps, side wrapping elements, wings and ears.

II. Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pyjamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polypropylene and/or polyethylene or combinations thereof as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spun-bonded nonwoven layer made from synthetic non-cellulose based fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious layer (B) is made of nonwoven comprising hydrophobic materials, e.g. synthetic non-cellulose based fibers or a liquid-impervious polymeric film comprising plastics e.g. polyethylene and/or polypropylene and/or combinations thereof. The thickness of the liquid-impervious layer is preferably 12 to 30 µm.

Further, the liquid-impervious layer (B) is preferably made of a laminate of nonwoven and plastics comprising a nonwoven having a density of 12 to 15 gsm and a polyethylene layer having a thickness of about 10 to 20 µm.

The typical liquid-impervious layer (B) extends partially or wholly across the fluid-absorbent structure and can extend into and/or form part of all the preferred sideflaps, side wrapping elements, wings and ears.

III. Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

The top view area of the fluid-absorbent core of a maxi size/L/4 baby diaper (C) is preferably at least 200 cm$^2$, more preferably at least 250 cm$^2$, most preferably at least 300 cm$^2$. The top view area is the part of the core that is face-to-face to the upper liquid-pervious layer.

Furthermore the fluid-absorbent core according to the present invention can include the following components:
1. an optional core cover
2. a fluid storage layer
3. an optional dusting layer 1. Optional Core Cover In order to increase the integrity of the fluid-absorbent core, the core is provided with a cover. This cover may be at the top and/or at the bottom of the fluid-absorbent core. Further, this cover may include the whole fluid-absorbent core with a unitary sheet of material and thus function as a wrap. Wrapping is possible as a full wrap, a partial wrap or as a C-Wrap.

The material of the core cover may comprise any known type of substrate, including webs, garments, textiles, films, tissues and laminates of two or more substrates or webs. The core cover material may comprise natural based fibers, such as cellulose, cotton, flax, linen, hemp, wool, silk, fur, hair and naturally occurring mineral fibers. The core cover material may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the core cover comprises synthetic non-cellulose based fibers or tissue.

The fibers may be mono- or multicomponent. Multicomponent fibers may comprise a homopolymer, a copolymer or blends thereof.

2. Fluid-Storage Layer

The fluid-absorbent compositions included in the fluid-absorbent core comprise fibrous materials and fluid-absorbent polymer particles.

Fibers useful in the present invention include natural cellulose based fibers and synthetic non-cellulose based fibers. Examples of suitable modified or unmodified natural cellulose based fibers are given in the chapter "Liquid-pervious Layer (A)" above. From those, wood pulp fibers are preferred.

Examples of suitable synthetic non-cellulose based fibers are given in the chapter "Liquid-pervious Layer (A)" above.

The fibrous material may comprise only natural cellulose based fibers or synthetic non-cellulose based fibers or any combination thereof.

The fibrous material as a component of the fluid-absorbent compositions may be hydrophilic, hydrophobic or can be a combination of both hydrophilic and hydrophobic fibers.

Generally for the use in a fluid-absorbent core, which is the embedded between the upper layer (A) and the lower layer (B), hydrophilic fibers are preferred. This is especially the case for fluid-absorbent compositions that are desired to quickly acquire, transfer and distribute discharged body fluids to other regions of the fluid-absorbent composition or fluid-absorbent core. The use of hydrophilic fibers is especially preferred for fluid-absorbent compositions comprising fluid-absorbent polymer particles.

Examples for hydrophilic fibers are given in the chapter "Liquid-pervious Layer (A)" above. Preferably, the fluid-absorbent core is made from viscose acetate, polyester and/or polypropylene.

The fibrous material of the fluid-absorbent core may be uniformly mixed to generate a homogenous or inhomogenous fluid-absorbent core. Alternatively the fibrous material may be concentrated or laid in separate layers optionally comprising fluid-absorbent polymer material. Suitable storage layers of the fluid-absorbent core comprising homogenous mixtures of fibrous materials comprising fluid-absorbent polymer material. Suitable storage layers of the fluid-absorbent core including a layered core-system comprise homogenous mixtures of fibrous materials and comprise fluid-absorbent polymer material, whereby each of the layers may be built from any fibrous material by means known in the art. The sequence of the layers may be directed such that a desired fluid acquisition, distribution and transfer results, depending on the amount and distribution of the inserted fluid-absorbent material, e.g. fluid-absorbent polymer particles. Preferably there are discrete zones of highest absorption rate or retention within the storage layer of the fluid-absorbent core, formed of layers or inhomogenous mixtures of the fibrous material, acting as a matrix for the incorporation of fluid-absorbent polymer particles. The zones may extend over the full area or may form only parts of the fluid-absorbent core.

Suitable fluid-absorbent cores comprise fibrous material and fluid-absorbent material. Suitable is any fluid-absorbent material that is capable of absorbing and retaining body fluids or body exudates such as cellulose wadding, modified and unmodified cellulose, crosslinked cellulose, laminates, composites, fluid-absorbent foams, materials described as in the chapter "Liquid-pervious Layer (A)" above, fluid-absorbent polymer particles and combinations thereof.

Typically the fluid-absorbent cores may contain a single type of fluid-absorbent polymer particles or may contain fluid-absorbent polymer particles derived from different kinds of fluid-absorbent polymer material. Thus, it is possible to add fluid-absorbent polymer particles from a single kind of polymer material or a mixture of fluid-absorbent polymer particles from different kinds of polymer materials, e.g. a mixture of regular fluid-absorbent polymer particles, derived from gel polymerization with fluid-absorbent polymer particles, derived from droplet polymerization. Alternatively it is possible to add fluid-absorbent polymer particles derived from inverse suspension polymerization.

Alternatively it is possible to mix fluid-absorbent polymer particles showing different feature profiles. Thus, the fluid-absorbent core may contain fluid-absorbent polymer particles with uniform pH value, or it may contain fluid-absorbent polymer particles with different pH values, e.g. two- or more component mixtures from fluid-absorbent polymer particles with a pH in the range from about 4.0 to about 7.0. Preferably, applied mixtures deriving from mixtures of fluid-absorbent polymer particles got from gel polymerization or inverse suspension polymerization with a pH in the range from about 4.0 to about 7.0 and fluid-absorbent polymer particles got from droplet polymerization.

Suitable fluid-absorbent cores are also manufactured from loose fibrous materials by adding fluid-absorbent particles and/or fluid-absorbent polymer fibers or mixtures thereof. The fluid-absorbent polymer fibers may be formed from a single type of fluid-absorbent polymer fiber or may contain fluid-absorbent polymer fibers from different polymeric materials. The addition of fluid-absorbent polymer fibers may be preferred for being distributed and incorporated easily into the fibrous structure and remaining better in place than fluid-absorbent polymer particles. Thus, the tendency of gel blocking caused by contacting each other is reduced. Further, fluid-absorbent polymer fibers are softer and more flexible.

In the process of manufacturing the fluid-absorbent core, fluid-absorbent polymer particles and/or fluid-absorbent fibers are brought together with structure forming compounds such as fibrous matrices. Thus, the fluid-absorbent polymer particles and/or fluid-absorbent fibers may be added during the process of forming the fluid-absorbent core from loose fibers. The fluid-absorbent core may be formed by mixing fluid-absorbent polymer particles and/or fluid-absorbent fibers with fibrous materials of the matrix at the same time or adding one component to the mixture of two or more other components either at the same time or by continuously adding.

Suitable fluid-absorbent cores including mixtures of fluid-absorbent polymer particles and/or fluid-absorbent fibers and fibrous material building matrices for the incorporation of the fluid-absorbent material. Such mixtures can be formed homogenously, that is all components are mixed together to get a homogenous structure. The amount of the fluid-absorbent materials may be uniform throughout the fluid-absorbent core, or may vary, e.g. between the central region and the distal region to give a profiled core concerning the concentration of fluid-absorbent material. Suitable fluid absorbent cores are described e.g. in WO 2010002828 A1, WO 2004 073571 and WO 2010 133529.

Techniques of application of the fluid-absorbent polymer materials into the absorbent core are known to persons skilled in the art and may be volumetric, loss-in-weight or gravimetric. Known techniques include the application by vibrating systems, single and multiple auger systems, dosing roll, weigh belt, fluid bed volumetric systems and gravitational sprinkle and/or spray systems. Further techniques of insertion are falling dosage systems consensus and contradictory pneumatic application or vacuum printing method of applying the fluid absorbent polymer materials.

Suitable fluid-absorbent cores may also include layers, which are formed by the process of manufacturing the fluid-absorbent article. The layered structure may be formed by subsequently generating the different layers in height (z-direction).

Alternatively a core-structure can be formed from two or more preformed layers to get a layered fluid-absorbent core. The layers may have different concentrations of fluid-absorbent polymer material showing concentrations in the range from about 20 to 95%. These uniform or different layers can be fixed to each other at their adjacent plane surfaces. Alternatively, the layers may be combined in a way that a plurality of chambers are formed, in which separately fluid-absorbent polymer material is incorporated.

Suitable preformed layers are processed as e.g. air-laid, wet-laid, laminate or compos-ite structure.

Alternatively layers of other materials can be added, e.g. layers of opened or closed celled foams or perforated films. Included are also laminates of at least two layers comprising said fluid-absorbent polymer material.

Further a composite structure can be formed from a carrier layer (e.g. a polymer film), onto which the fluid-absorbent polymer material is affixed. The fixation can be done at one side or at both sides. The carrier layer may be pervious or impervious for body-fluids.

Alternatively, it is possible to add monomer solution after the formation of a layer or onto a carrier layer and polymerize the coating solution by means of UV-induced polymerization technologies. Thus, "in situ"-polymerization is a further method for the application of fluid-absorbent polymers.

Thus, suitable fluid-absorbent cores comprising at least 60% by weight fluid-absorbent polymer particles and not more than 40% by weight of cellulose based fibers, preferably at least 70% by weight fluid-absorbent polymer particles and not more than 30% by weight of cellulose based fibers, more preferably 80% by weight fluid-absorbent polymer particles and not more than 20% by weight of cellulose based fibers, most preferably at least 90% by weight fluid-absorbent polymer particles and not more than 10% by weight of cellulose based fibers, based on the fluid-absorbent core.

The quantity of fluid-absorbent polymer particles and/or fluid-absorbent fibers within the fluid-absorbent core is from 3 to 20 g, preferably from 6 to 14 g, and from 8 to 12 g in the case of maxi-diapers, and in the case of incontinence products up to about 50 g.

Typically fluid-absorbent articles comprising at least an upper liquid-pervious layer (A), at least a lower liquid-impervious layer (B) and at least one fluid-absorbent core between the layer (A) and the layer (B) besides other optional layers. In order to increase the control of body fluid absorption and/or to increase the flexibility in the ratio weight percentages of fluid-absorbent polymer particles to fibrous matrix it may be advantageous to add one or more further fluid-absorbent cores. The addition of a second fluid-absorbent core to the first fluid-absorbent core offers more possibilities in body fluid transfer and distribution. Moreover higher quantities of discharged body fluids can be retained. Having the opportunity of combining several layers showing different fluid-absorbent polymer concentration and content, it is possible to reduce the thickness of the fluid-absorbent article to a minimum even if there are several fluid-absorbent cores included.

Suitable fluid-absorbent cores may be formed from any material known in the art which is designed to acquire, transfer, and retain discharged body fluids. The technology of manufacturing may also be anyone known in the art. Preferred technologies include the application of monomer-solution to a transported fibrous matrix and thereby polymerizing, known as in-situ technology, or the manufacturing of air-laid composites.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of fluid-absorbent polymer particles and/or the distribution of the fluid-absorbent polymer particles and/or the dimensions of the different layers if a layered fluid-absorbent core is present.

It is known that absorbent cores providing a good wet immobilization by combining several layers, e.g. a substrate layer, layers of fluid-absorbent polymer and layers of thermoplastic material. Suitable absorbent cores may also comprise tissue or tissue laminates. Known in the art are single or double layer tissue laminates formed by folding the tissue or the tissue laminate onto itself.

These layers or foldings are preferably joined to each e.g. by addition of adhesives or by mechanical, thermal or ultrasonic bonding or combinations thereof. Fluid-absorbent polymer particles may be comprised within or between the individual layers, e.g. by forming separate fluid-absorbent polymer layers.

Thus, according to the number of layers or the height of a voluminous core, the resulting thickness of the fluid-absorbent core will be determined. Thus, fluid-absorbent cores may be flat as one layer (plateau) or have three-dimensional profile.

Generally the upper liquid-pervious layer (A) and the lower liquid-impervious layer (B) may be shaped and sized according to the requirements of the various types of fluid-absorbent articles and to accommodate various user/wearer's size. Thus, the combination of the upper liquid-pervious layer and the lower liquid-impervious layer may have all dimensions or shapes known in the art. Suitable combinations have an hourglass shape, rectangular shape, trapezoidal shape, t- or double t-shape or showing anatomical dimensions.

The fluid-absorbent core may comprise additional additives typically present in fluid-absorbent articles known in the art. Exemplary additives are fibers for reinforcing and stabilizing the fluid-absorbent core. Preferably polyethylene is used for reinforcing the fluid-absorbent core.

Further suitable stabilizers for reinforcing the fluid-absorbent core are materials acting as binder.

In varying the kind of binder material or the amount of binder used in different regions of the fluid-absorbent core it is possible to get a profiled stabilization. For example, different binder materials exhibiting different melting temperatures may be used in regions of the fluid-absorbent core, e.g. the lower melting one in the central region of the core, and the higher melting in the distal regions. Suitable binder materials may be adhesive or non-adhesive fibers, continuously or discontinuously extruded fibers, bi-component staple fibers, non-elastomeric fibers and sprayed liquid binder or any combination of these binder materials.

Further, thermoplastic compositions usually are added to increase the integrity of the core layer. Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefin or styrene block copolymer and mixture of waxes.

Suitable thermoplastic polymers are styrenic block copolymers including A-B-A triblock segments, A-B diblock segments and $(A-B)_n$ radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyal-phaolefins and metallocene polyolefins.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with acid groups such as ascorbic, benzoic, citric, salicylic or sorbic acid and fluid-soluble polymers of monomers with acid groups, homo- or co-polymers of $C_3$-$C_5$ mono-unsaturated carboxylic acids.

Suitable odor control additives are further perfumes such as allyl caproate, allyl cyclo-hexaneacetate, allyl cyclo-hexanepropionate, allyl heptanoate, amyl acetate, amyl propionate, anethol, anixic aldehyde, anisole, benzaldehyde, benzyl acetete, benzyl acetone, benzyl alcohol, benzyl butyrate, benzyl formate, camphene, camphor gum, laevocarveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, Zn; enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from about 0.5 to about 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of about 0.01 to 0.5% by weight related to the weight of the fluid-absorbent core.

The bulk density of the fluid-absorbent core is in the range of 0.12 to 0.35 g/cm$^3$. The thickness (z-dimension) of the fluid-absorbent core is in the case of diapers in the range of 1 to 6 mm, preferably 1.5 to 3 mm, in the case of incontinence products in the range of 3 to 15 mm.

3. Optional Dusting Layer

An optional component for inclusion into the absorbent core is a dusting layer adjacent to. The dusting layer is a fibrous layer and may be placed on the top and/or the bottom of the absorbent core. Typically, the dusting layer is underlying the storage layer. This underlying layer is referred to as a dusting layer, since it serves as carrier for deposited fluid-absorbent polymer particles during the manufacturing process of the fluid-absorbent core. If the fluid-absorbent polymer material is in the form of macrostructures, films or flakes, the insertion of a dusting layer is not necessary. In the case of fluid-absorbent polymer particles derived from droplet polymerization, the particles have a smooth surface with no edges. Also in this case, the addition of a dusting layer to the fluid-absorbent core is not necessary. On the other side, as a great advantage the dusting layer provides some additional fluid-handling properties such as wicking performance and may offer reduced incidence of pin-holing and or pock marking of the liquid-impervious layer (B).

Preferably, the dusting layer is a fibrous layer comprising fluff (cellulose based fibers), most preferably the dusting layer is non-cellulose based material such as spun-melt-spun (SMS), spun-bond, SMMS combinations and thermalbond polypropylene contacting the formation area and/or marrying the fluid absorbent immediately upon exit from the forming chamber before compression. Hot-melt adhesive is also employed to bond the non-cellulose fibre dusting layer to the core and/or bonding between the non-cellulose fibre based dusting following lamination or wrapping techniques know to people skilled in the art.

IV. Acquisition-Distribution Layer (D)

The acquisition-distribution layer (D) is located between the upper layer (A) and the fluid-absorbent core (C) and is preferably constructed to efficiently acquire discharged body fluids and to transfer and distribute them to other regions of the fluid-absorbent core, where the body fluids are immobilized and stored. Thus, the upper layer transfers the discharged liquid to the acquisition-distribution layer (D) for distributing it to the fluid-absorbent core.

In case of diapers the length of the acquisition-distribution layer is in its longitudinal direction shorter than the fluid-absorbing core. The length of the acquisition-distribution layer is in its longitudinal direction typically at least 50%, preferred at least 60%, more preferred at least 62.5% of the length of the fluid-absorbent core.

Typically the acquisition-distribution layer is not centered on the fluid-absorbing core. The distance between the centers of the fluid-absorbent core and the acquisition-distribution layer is typically from 5 to 20%, preferably from 8 to 18%, more preferably from 9 to 17% most preferred 10 to 16% of the total length of the fluid-absorbent core.

A typical acquisition-distribution layer may comprise a high loft synthetic fiber carded web which may be further bonded by air, calendaring and/or other modifications e.g. resin additive.

The acquisition-distribution layer comprises fibrous material and optionally fluid-absorbent polymer particles.

The fibrous material may be hydrophilic, hydrophobic or can be a combination of both hydrophilic and hydrophobic fibers. It may be derived from synthetic non-cellulose based fibers alone or in combination with not more than 10% by weight of natural cellulose based fibers, based on the sum of synthetic non-cellulose based fibers and cellulose based fibers.

Suitable acquisition-distribution layers are formed from synthetics alone, or synthetics in combination with not more than 10% by weight of cellulose based fibers and/or modified cellulose based fibers, based on the sum of synthetic non-cellulose based fibers and cellulose based fibers.

Multiple fiber types and combinations thereof can be employed, for example polyester, co-polyester, polypropylene along with optimization of the fiber dtex, preferred are e.g. 6-7 dtex for polyester and for copolyester with basis weight of 40-60 gsm, or for light incontinence acquisition-distribution layer e.g. a bi-component fibrous web of polypropylene and polyethylene with 3.3 dtex and 3.2 dtex respectively.

Examples of further suitable hydrophilic, hydrophobic fibers especially synthetic non-cellulose based fibers, as well as modified or unmodified natural cellulose based fibers are given in the chapter "Liquid-pervious Layer (A)" above.

For providing improved fluid acquisition and distribution properties suitable acquisition-distribution layers according to the invention comprise synthetic non-cellulose based fibers and optionally cellulose based fibers, whereas modified cellulose based fibers are preferred.

Examples for modified cellulose based fibers are chemically treated cellulose based fibers, especially chemically stiffened cellulose based fibers. The term "chemically stiffened cellulose based fibers" means cellulose based fibers that have been stiffened by chemical means to increase the stiffness of the fibers. Such means include the addition of chemical stiffening agent in the form of coatings and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulose based fibers may be stiffened by crosslink bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulose based fibers are chemically treated cellulose based fibers.

Examples of synthetic non-cellulose based fibers are found in the Chapter "Liquid-pervious Layer (A)" above.

Hydrophilic synthetic non-cellulose based fibers are preferred.

Especially preferred are polyester, polyethylene, polypropylene, polylactic acid, polyamides and/or blends thereof.

Hydrophilic synthetic non-cellulose based fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Suitable acquisition-distribution layers may comprise fibrous material and fluid-absorbent polymer particles distributed within. The fluid-absorbent polymer particles may be added during the process of forming the layer from loose fibers, or, alternatively, it is possible to add monomer solution after the formation of the layer and polymerize the coating solution by means of UV-induced polymerisation technologies. Thus, "in situ"-polymerisation is a further method for the application of fluid-absorbent polymers.

V. Optional Tissue Layer (E)

An optional tissue layer is disposed immediately above and/or below (C).

The material of the tissue layer may comprise any known type of substrate, including webs, garments, textiles and films. The tissue layer may comprise natural cellulose based fibers, such as cotton, flax, linen, hemp, wool, silk, fur, hair and naturally occurring mineral fibers. The tissue layer may also comprise synthetic non-cellulose based fibers such as rayon and lyocell (derived from cellulose), polysaccharides (starch), polyolefin fibers (polypropylene, polyethylene), polyamides, polyester, butadiene-styrene block copolymers, polyurethane and combinations thereof. Preferably, the tissue layer comprises cellulose based fibers. The optional tissue layer may be 'open' allowing passage of air through the substrate or 'closed' not allowing air passage through the substrate material.

VI. Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-meltblown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands.

Preferred are leg cuffs from synthetic non-cellulose based fibers showing the layer combinations sms, smms or smsms. Preferred are nonwovens with the density of 7 to 17 gsm. Preferably leg cuffs are provided with two elastic strands.

2. Elastics

The elastics are used for securely holding and flexibly closing the fluid-absorbent article around the wearer's body, e.g. the waist and the legs to improve containment and fit.

Leg elastics are placed between the outer and inner layers or the fluid-absorbent article, or between the outer cover and the bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elasticized or shrunk, e.g. by the application of heat.

3. Closure System

The closure system include tape tabs, landing zone, elastomerics, pull ups with refastenable side sections and the belt system.

At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate, acrylate or ethylene acrylic acid copolymers.

Suitable closing systems comprise further a hook portion of a hook and loop fastener and the target devices comprise the loop portion of a hook and loop fastener.

Suitable mechanical closing systems include a landing zone. Mechanical closing sys-tems may fasten directly into the outer cover. The landing zone acts as an area of the fluid-absorbent article into which it is desirable to engage the tape tabs. The base material may include a loop material. The loop material may include a backing material and a layer of a non-woven spunbond web attacked to the backing material.

Thus suitable landing zones can be made by spunbonding, spunbonded nonwovens are made from melt-spun fibers formed by extruding molten thermoplastic material. An example is bi-oriented polypropylene (BOPP), most preferred are brushed/closed loop in the case of prevalent mechanical closure systems.

Further, suitable mechanical closing systems including elastic units serving as a flexible waist band or side panels for fluid-absorbents articles, such as pants or pull-ups. The elastic units enable the wearer to pull down the fluid-absorbent article as e.g. a training pant or mobile user adult incontinence fluid absorbent article.

Suitable pants-shaped fluid-absorbent article has front section, rear section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer.

Suitable pull-ups comprising thermoplastic films, sheets and laminates have a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprise two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomeric material, thus providing a conformable fit of the fluid-absorbent article and maintaining adequate performance against leakage.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single fluid-absorbent core-system.

Suitable fluid-storage layers of the fluid-absorbent core comprising homogenous or inhomogenous mixtures of fibrous materials comprising fluid-absorbent polymer particles homogenously or inhomogenously dispersed in it.

Suitable fluid-storage layers of the fluid-absorbent core including a layered fluid-absorbent core-system comprising homogenous mixtures of fibrous materials and optionally comprising fluid-absorbent polymer particles, whereby each of the layers may be prepared from any fibrous material by means known in the art.

Preferably the fluid-absorbent core comprises at least 60% by weight of fluid-absorbent polymer particles and not more than 40% by weight of cellulose based fibers, based on the sum of fluid-absorbent polymer particles and cellulose based fibers.

According to the invention it is preferred, that the fluid-absorbent core is covered by an acquisition-distribution layer comprising at least 90% by weight of synthetic non-cellulose based fibers and not more than 10% by weight of cellulose based fibers, based on the sum of synthetic non-cellulose based fibers and cellulose based fibers.

Preferably the acquisition-distribution layer is in longitudinal direction asymmetric positioned on the fluid-absorbent core.

Especially preferred are fluid-absorbent articles having a diaper construction as explained above, wherein the acquisition-distribution layer is essentially free of cellulose based fibers.

It is preferred, that the thickness (z-dimension) of the acquisition-distribution layer is not more than 60% of the thickness of the fluid-absorbent core and the thickness deviation of the bi-folded fluid-absorbent article in longitudinal direction is less than 10%.

Preferable the thickness of the unfolded fluid-absorbent article is less than 3 mm.

The distance between the centers of the fluid-absorbent core and the acquisition-distribution layer is from 5 to 20%, preferably from 10 to 16% of the total length of the fluid-absorbent core.

It is preferred that the synthetic non-cellulose based fibers are based on polyester, polyethylene, polypropylene, polylactic acid, polyamide and/or blends thereof.

Furthermore the fluid-absorbent core may be encapsulated by wrapping with a nonwoven material or a tissue paper.

The fluid-absorbent core comprises at least 80% by weight of water-absorbent polymer particles and less than 10% by weight of cellulose based fibers.

It is preferred, e.g. for a homogeneous distribution of the water-absorbent polymer particles to place them in discrete regions of the fluid-absorbent core.

The amount of water-absorbent polymer particles included in the absorbent core is at least 8 g. The particles preferably have a bulk density of at least 0.55 g/cm$^3$ and a centrifuge retention capacity of at least 24 g/g, an absorbency under high load of at least 18 g/g and a saline flow conductivity of at least 20×10$^{-7}$ cm$^3$ s/g.

In order to immobilize the fluid-absorbent polymer particles, the adjacent layers are fixed by the means of thermoplastic materials, thereby building connections throughout the whole surface or alternatively in discrete areas of junction.

For the latter case, cavities or pockets are built carrying the fluid-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products fluid-absorbent core and the components contained therein is made and controlled by the discrete application of hotmelt adhesives as known to people skilled in the art. Examples would be e.g. Dispomelt 505B, Dispomelt Cool 1 101, as well as other specific function adhesives manufactured by for example Henkel, Fuller, Colchimica or Bostik.

Methods

The measurements should unless stated otherwise, be carried out at an ambient temperature of 23±2° C. and an atmospheric humidity of 50±10%. The fluid absorbent polymers are mixed thoroughly before the measurement.

Density of the Fluid-Absorbing Polymer Particles

The apparent density, also known as bulk density, of the absorbent polymer material, typically in particle form, can be measured according to the standard INDA-EDANA test method WSP 260.2 (05), wherein the test conditions, referred to under Section 6.2 of the standard test method, are to be set as 23±2° C. and a humidity of 50±5%.

Saline Flow Conductivity (SFC)

The saline flow conductivity is, as described in EP 0 640 330 A1, determined as the gel layer permeability of a swollen gel layer of fluid-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

$$SFC[cm^3\ s/g] = (Fg(t=0) \times L0)/(d \times A \times WP),$$

where $Fg(t=0)$ is the flow rate of NaCl solution in g/s, which is obtained by means of a linear regression analysis of the $Fg(t)$ data of the flow determinations by extrapolation to $t=0$, LO is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

Centrifuge Retention Capacity (CRC)

The centrifuge retention capacity of the fluid-absorbent polymer particles is determined by the EDANA recommended test method No. WSP 241.3-10 "Centrifuge Retention Capacity", wherein for higher values of the centrifuge retention capacity larger tea bags have to be used due to bursting of the tea-bag upon hydration.

Free Swell Gel Bed Permeability (GBP)

The method for determination of the Free Swell Gel Bed Permeability (Free Swell GBP) is described in US patent application no. US 2005/0256757 A1, paragraphs [0061] to [0075].

Absorbency Under High Load (AUHL)

The absorbency under high load of the fluid-absorbent polymer particles is determined analogously to the EDANA recommended test method No. WSP 242.3-10 "Absorption Under Pressure", except using a weight of 49.2 g/cm$^2$ instead of a weight of 21.0 g/cm$^2$.

Moisture Content

The moisture content of the fluid-absorbent polymer particles is determined by the EDANA recommended test method No. WSP 230.3-10 "Moisture Content".

Residual Monomers

The level of residual monomers in the fluid-absorbent polymer particles is determined by the EDANA recommended test method No. WSP 210.3-10 "Residual Monomers".

Particle Size Distribution

The particle size distribution of the fluid-absorbent polymer particles is determined with EDANA recommended test method No. 220.3.10 "Particle size distribution by sieve fractionation"

Extractables

The level of extractable constituents in the fluid-absorbent polymer particles is determined by the EDANA recommended test method No. WSP 270.2-05 "Extractables".

The EDANA test methods are obtainable, for example, from the EDANA, Avenue Eugène Plasky 157, B-1030 Brussels, Belgium.

Thickness-Measurement of Fluid-Absorbent Articles

Scope of the thickness test is the determination of the height (z-dimension) of a fluid-absorbent article, here a diaper. For determining the height of a diaper, the thickness of the diaper is measured at certain points that are marked out on the article.

Materials that are needed for carrying out the thickness test are 20 diapers to be tested, a ruler and a portable thickness gauge M 258b Model J100 of 0.01 mm graduation with a feeler size of 30 mm diameter and a measuring pressure of 0.113 N/cm², available from SDL Atlas United Kingdom, P.O. Box 162, Crown Royal Shawcross St., Stockport SK1 3JW England.

A. Measuring the Thickness of the Bi-Folded Diaper

Figure 1:
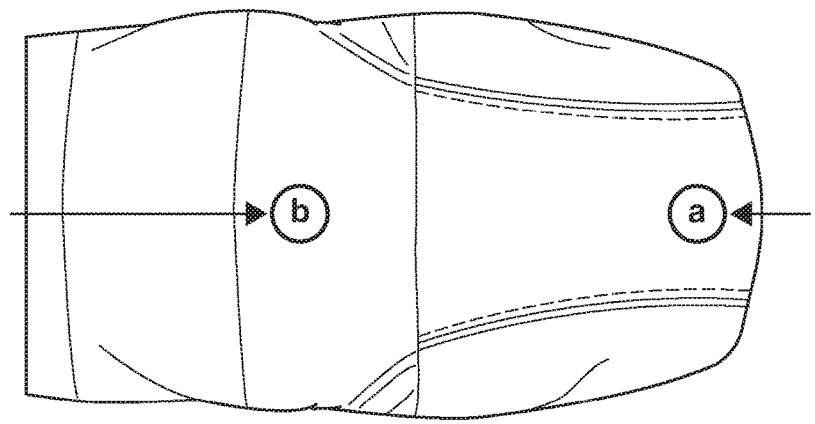
FIG. 1 shows a bi-folded diaper

At first, the thickness of the folded diaper is determined. The diaper is folded such that each longitudinal side is folded inward towards the crotch and then the diaper is folded once at the centre so that it overlaps itself. The so folded diaper is placed with front side upwards onto the table indicated by presence of frontal tape zone for marrying with closure tapes when applying the diaper to user; see FIG. 1. FIG. 1 shows the measuring points (a, b) on the bi-folded diaper.

Two measuring points a) and b) are marked out on the folded diaper on a centre line in longitudinal direction at the following distances from the bi-fold and from the (opposite) waistband end of the diaper (see FIG. 1). The centre line runs through the diaper on half of the length of the diaper in transverse ($L_T$) direction. Measuring point (a) is in a distance of 2.0 cm (center of the feeler) from the fold and measuring point (b) is in a distance of 8.0 cm (center of the feeler) from the waistband end of the folded diaper.

The thickness of the diaper at each measuring point has been determined three times with the portable thickness gauge from SDL Atlas. The resulting value is the average value of the three measurements at each noted location (a and b) on the folded diaper.

The thickness deviation of the bi-folded diaper in longitudinal direction was calculated according to the following equation:

$$\text{Thickness deviation} = 1\left[\frac{\text{Thickness at point }(b)}{\text{Thickness at point }(a)}\right] \times 100$$

B. Determination of the Centre and Measuring the Thickness of a Diaper or ADL or Core Respectively, in Unfolded Form To measure the thickness of a diaper in unfolded form, the diaper is placed in unfolded form backsheet garment contact surface upwards (user contact surface side down) onto an inspection table. The unfolded diaper is schematically shown in FIG. 2 with reference number 1 marking the front end, number 2 the rear of the diaper and 3 the core of the diaper.

Figure 2:
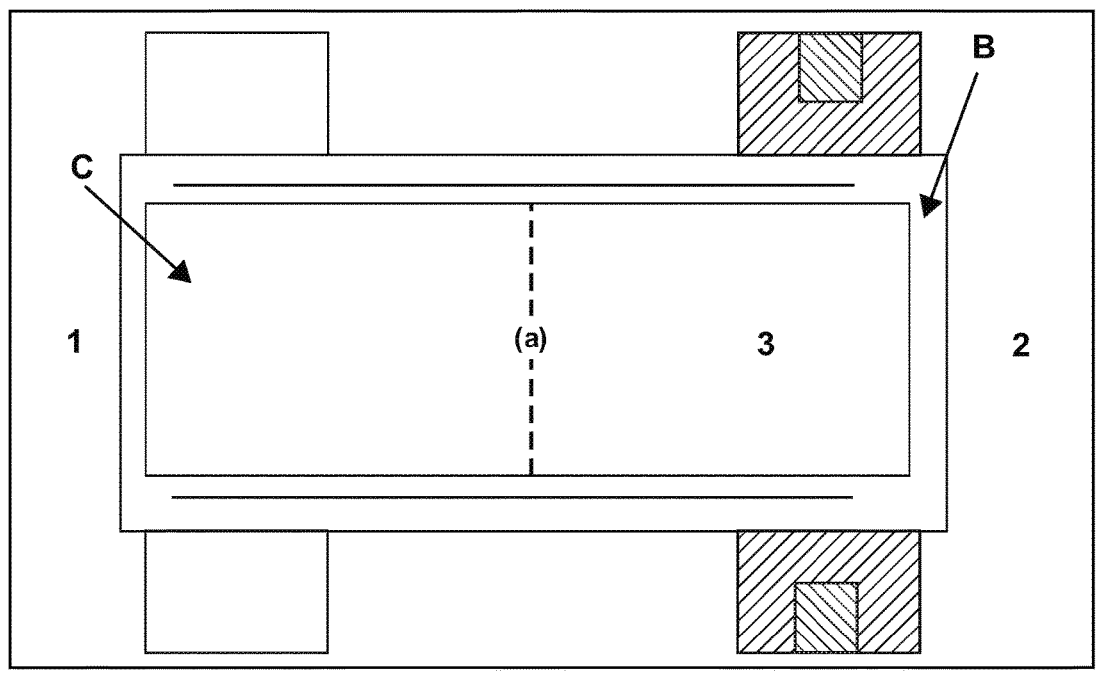
FIG. 2 shows a schematic top view of an unfolded diaper

One measuring point (a) central (center) are marked out on the opened diaper as shown on FIG. 2. To determine the center (a) the length of the diaper in both longitudinal ($L_{Lo}$) and transverse ($L_T$) direction is measured. The central point (a) is at $L_{Lo}/2$ and $L_T/2$.

As described above measuring point (a) (center of the feeler) is located directly in the centre of the diaper.

The thickness of the diaper at the measuring point has been determined three times with the portable thickness gauge from SDL Atlas. The resulting value is the average value of the three measurements at each noted location (a) on the unfolded diaper.

The center and the thickness of the core and of the acquisition distribution layer are determined accordingly.

Acquisition Rate Under Load and Rewet Under Load

The combined acquisition rate under load is the determination of the time needed for the diaper to completely absorb a certain amount of synthetic urine to ensure dryness of the diaper even in gush situations and the rewet under load test is the determination of the dryness of a diaper under a certain load. For testing a fluid-absorbent article, in this case a diaper, the diaper is insulted several times with defined amounts of synthetic urine under a load. Synthetic urine consists of a 9 g/l solution of sodium chloride in deionised water with a surface tension of (70±2) mN/m. The rewet under load is measured by the amount of fluid the article releases after being maintained at a pressure of 0.7 psi for 10 min after commencement of each insult.

Materials and apparatus that are needed for carrying out the acquisition rate and rewet under load test are an a 3.64 kg (±0.0075 kg) circular 0.7 psi (±0.01 psi) weight with a diameter of 10 cm, with 2.38 cm ID perspex dose tube through the center of the weight, a 2.5 kg circular weight (0.7 psi) with a diameter of 8 cm, filter papers Whatman® No. 1 with 9 cm diameter or equivalent ones, a digital timer, an electronic balance (accuracy of 0.01 g), beakers, a ruler and a separatory funnel with a flow rate set at 7 g/sec±1 sec or equivalent.

At first the weight of the fluid-absorbent article to be tested is recorded.

The article is placed flat on e.g. an inspection table, for example by using clamps or by taping the ends of the article to the respective table. The article is placed nonwoven side up onto the inspection table orientated with back of the article clamped furthest away.

An insult point is marked out on the article. The point should be positioned accordingly with regard to the type and gender of the diaper to be tested, e.g. it was positioned 2.5 cm towards the front from centre of the core for unisex diapers, in the centre of the core for girl diapers and 5 cm toward the front for boy diapers to be tested.

To perform the test under load, the 3.64 kg load (±0.0075 kg) is placed onto the fluid-absorbent article with the opening of the perspex tube positioned centrally at the previously marked insult point.

As the size of the fluid-absorbent article determines the amount of fluid the fluid-absorbent article could be insulted with, defined amounts of synthetic urine for each insult has to be chosen. The amount of synthetic urine for different types of diapers is summarized in Table 1.

TABLE 1

Amount of synthetic urine per insult

| Product Size | Primary Insult (g) | Secondary Insult (g) | Tertiary Insult (g) | Fourth Insult (g) | Fifth Insult (g) | Additional Insults (g) |
|---|---|---|---|---|---|---|
| Mini | 80 | 40 | 40 | 40 | 40 | 40 |
| Midi | 80 | 40 | 40 | 40 | 40 | 40 |
| Maxi | 100 | 50 | 50 | 50 | 50 | 50 |
| Maxi Plus | 100 | 50 | 50 | 50 | 50 | 50 |
| Junior | 100 | 50 | 50 | 50 | 50 | 50 |

TABLE 1-continued

Amount of synthetic urine per insult

| Product Size | Primary Insult (g) | Secondary Insult (g) | Tertiary Insult (g) | Fourth Insult (g) | Fifth Insult (g) | Additional Insults (g) |
|---|---|---|---|---|---|---|
| Large | 100 | 50 | 50 | 50 | 50 | 50 |
| Adult Inco. | 150 | 150 | 150 | 150 | 150 | 150 |

For the primary insult the respective amount of synthetic urine is weighed into a beaker, poured into the perspex tube and the timer is started immediately as soon as the fluid is released onto the fluid-absorbent article. The time (A1) in seconds, for the fluid to be fully absorbed into the article is recorded.

After 10 minutes the load was removed and the rewet procedure is performed.

The amount of filter paper used varies with the product size see table 2, e.g. for a diaper with product size "maxi" the number of filter paper to be used for the primary insult is 10.

TABLE 2

Number of filter papers per insult.

| Product Size | Primary Rewet | Secondary Rewet | Tertiary Rewet | Fourth Rewet | Fifth Rewet |
|---|---|---|---|---|---|
| Mini | 10 | 20 | 30 | 40 | 50 |
| Midi | 10 | 20 | 30 | 40 | 50 |
| Maxi | 10 | 20 | 30 | 40 | 50 |
| Maxi Plus | 10 | 20 | 30 | 40 | 50 |
| Junior | 10 | 20 | 30 | 40 | 50 |
| Large | 10 | 20 | 30 | 40 | 50 |
| Adult Inco. | 20 | 40 | 60 | 80 | 100 |

The correct amount of filter papers for the product size (see table 2) is weighed out, this value is the dry weight (First insult—D1).

The stack of filter papers was placed centred over the insult point on the fluid-absorbent article and a 2.5 kg weight was placed onto the filter papers for 2 min.

The filter papers were reweighed and the resulting value is the wet weight ($W1_{first\ insult}$) for the first insult.

The acquisition rate under load equipment is replaced back onto the article immediately after removal of filter papers and rewet weight in the same position as before and the procedure is repeated for further insults and rewet tests. For each further insult the respective amount of artificial urine is used according to table 3 and the corresponding acquisition time (A2, A3, A4, A5) recorded. Furthermore the respective number (table 2) of filter papers is weighed out (Secondary Insult—D2, Tertiary Insult—D3, Quaternary/Fourth Insult—D4, Pentiary/Fifth Insult—D5) and the respective wet weights $W2_{secondary\ insult}$, $W3_{tertiary\ insult}$, $W4_{fourth\ insult}$, $W5_{fifth\ insult}$ are recorded.

The rewet under load is calculated according to the following equations $$\text{Rewet under load}_{first\ insult}(g) = (W1_{first\ insult}) - (D1)$$

$$\text{Rewet under load}_{secondary\ insult}(g) = (W2_{secondary\ insult}) - (D2)$$

$$\text{Rewet under load}_{tertiary\ insult}(g) = (W3_{tertiary\ insult}) - (D3)$$

$$\text{Rewet under load}_{fourth\ insult}(g) = (W4_{fourth\ insult}) - (D4)$$

$$\text{Rewet under load}_{fifth\ insult}(g) = (W5_{fifth\ insult}) - (D5)$$

$$\text{Rewet under load}_{x\ insult}(g) = (WX_{x\ insult}) - (DX)$$

The acquisition rate under load is calculated according to the following equations:

$$\text{Acquisition rate (g/sec)} = \frac{100[g]}{A1[s]} \text{ for the primary insult}$$

$$\text{Acquisition rate (g/sec)} = \frac{50[g]}{A2[s]} \text{ for the secondary insult}$$

$$\text{Acquisition rate (g/sec)} = \frac{50[g]}{A3[s]} \text{ for the tertiary insult}$$

$$\text{Acquisition rate (g/sec)} = \frac{50[g]}{A4[s]} \text{ for the fourth insult}$$

$$\text{Acquisition rate (g/sec)} = \frac{50[g]}{A5[s]} \text{ for the fifth insult}$$

$$\text{Acquisition rate (g/sec)} = \frac{50[g]}{AX[s]} \text{ for the } X \text{ insult}$$

EXAMPLES

1. Acquisition Under Load and Rewet Under Load

Comparative Example

Diapers Pampers Active Fit size 4 (maxi)(Procter & Gamble, Germany), ADL 60 g/m² resin-bond are used as comparative example.

All diapers of a package were weighed and 4 diapers with a similar weight are chosen for the measurements. The acquisition and rewet under load were measured for up to 5 insults.

Acquisition Under Load

According to table 1 the amount of artificial urine used for the insults are as follows:

Primary Insult 100 g, Secondary Insult 50 g, Tertiary Insult 50 g, Fourth Insult 50 g, Fifth Insult 50 g The results are summarized in the following table

TABLE 3

Results Acquisition under load comparative example

| Weight of the diaper | acquisition time 1 for primary insult (s) | acquisition time 2 for secondary Insult (s) | acquisition time 3 for tertiary insult (s) | acquisition time 4 for fourth insult (s) | acquisition time 5 for fifth insult (s) |
|---|---|---|---|---|---|
| 31.53 | 55 | 54 | 72 | 86 | 107 |
| 31.57 | 53 | 54 | 71 | 90 | 95 |
| 31.60 | 53 | 52 | 68 | 84 | 94 |
| 31.63 | 51 | 51 | 61 | 75 | 85 |
| Average time (s): | 53 | 53 | 68 | 84 | 95 |
| Aquisition rate (g/s) | 1.89 | 0.95 | 0.74 | 0.60 | 0.52 |

The average aquisition rate is 0.84 g/s.

Rewet Under Load

The results are listed in the following table

TABLE 4

Results Rewet under load comparative example

| Weight of diaper (g) | Rewet 1 (g) | Rewet 2 (g) | Rewet 3 (g) | Rewet 4 (g) | Rewet 5 (g) | Total Rewet (g) |
|---|---|---|---|---|---|---|
| 31.53 | 0.04 | 0.11 | 0.47 | 5.27 | 11.12 | 17.01 |
| 31.57 | 0.06 | 0.07 | 0.41 | 8.51 | 13.20 | 22.25 |
| 31.60 | 0.06 | 0.02 | 0.21 | 5.48 | 15.69 | 21.46 |
| 31.63 | 0.07 | 0.01 | 0.41 | 12.90 | 13.78 | 27.17 |
| Average value (g): | 0.06 | 0.05 | 0.38 | 8.04 | 13.45 | 21.97 |

Inventive Example

Diapers Pampers Active Fit (Procter & Gamble, Germany) size 4 (maxi), ADL Texsus, Italy AB2060, Air through bonded 60 g/m², Acquitex, Skin Side are used.

All diapers of a package were weighed and 4 diapers with a similar weight are chosen. Then the original ADL and the curly fibers are replaced by an ADL of Texsus, Italy. (Air through bonded 60 g/m², Acquitex, Skin Side) by carefully cutting open the coverstock of each diaper and removing the original ADL (60 g/m²) and the curly fiber of the diaper and then putting in the ADL of Texsus, which was tailored to fit in the diaper to replace the original ADL's size and location.

The coverstock was closed, laying it back on the ADL.

Then the acquisition and rewet under load was measured for each diaper for up to 5 insults.

Acquisition Under Load

According to table 1 the amount of artificial urine used for the insults are as follows:

Primary Insult 100 g, Secondary Insult 50 g, Tertiary Insult 50 g, Fourth Insult 50 g, Fifth Insult 50 g.

TABLE 5

Results Acquisition under load inventive example

| Weight of the diaper | acquisition time 1 (s) | Acquisition Time 2 (s) | acquisition time 3 (s) | acquisition time 4 (s) | acquisition time 5 (s) |
|---|---|---|---|---|---|
| 31.04 | 69 | 65 | 78 | 87 | 87 |
| 31.04 | 66 | 59 | 69 | 77 | 79 |
| 31.00 | 68 | 62 | 67 | 75 | 74 |
| 31.01 | 60 | 56 | 56 | 71 | 67 |
| Average (s): | 66 | 61 | 68 | 78 | 77 |
| Acquisition Rate (g/s): | 1.52 | 0.83 | 0.74 | 0.65 | 0.65 |

The average acquisition rate is 0.86 g/s

Rewet Under Load

According to table 1 the amount of artificial urine used for the insults are as follows:

Primary Insult 100 g, Secondary Insult 50 g, Tertiary Insult 50 g, Fourth Insult 50 g, Fifth Insult 50 g

TABLE 6

Results Rewet under load inventive example

| Weight of the diaper (g) | Rewet 1 (g) | Rewet 2 (g) | Rewet 3 (g) | Rewet 4 (g) | Rewet 5 (g) | Total Rewet (g) |
|---|---|---|---|---|---|---|
| 31.04 | 0.11 | 0.08 | 0.14 | 2.74 | 5.36 | 8.43 |
| 31.04 | 0.12 | 0.15 | 0.14 | 1.82 | 2.78 | 5.01 |
| 31.00 | 0.12 | 0.10 | 0.16 | 1.96 | 6.04 | 8.38 |
| 31.01 | 0.13 | 0.12 | 0.10 | 0.75 | 4.28 | 5.38 |
| Average rewet (g): | 0.12 | 0.11 | 0.14 | 1.82 | 4.62 | 6.80 |

The diaper according to the invention is drier in respect to rewet under load of the artificial urine (lower total rewet under load) than the tested commercial diaper.

The diaper according to the invention is slower in respect to acquisition of the artificial urine for the first 2 additions but faster for the 4$^{th}$ and 5$^{th}$ additions (acquisition rate under load) than the tested commercial diaper. The average acquisition rates under load are comparable for both diapers.

Thickness Measurements

Folded Diaper

Comparative Example

Diapers Pampers Active Fit, size 4 (maxi), ADL 60 g/m² Resinbond are used as comparative example.

All diapers of a package were weighed and 20 diapers with a similar weight are chosen for the measurements.

The measuring points (a) and (b) are marked out on the folded diaper on a centre line in longitudinal direction (see FIG. 1). Measuring point (a) is in a distance of 2.0 cm (center of the feeler) from the fold, measuring point (b) is in a distance of 8.0 cm (center of the feeler) from the waistband end of the folded diaper. The resulting value is the average value of the three measurements at each noted location (a and b) on the folded diaper.

TABLE 7

Thickness bi-folded comparative diaper

| Weight of the diaper (g) | Thickness (a) (mm) | Thickness (b) (mm) |
|---|---|---|
| 31.18 | 8.0 | 7.1 |
| 31.23 | 8.0 | 6.6 |
| 31.17 | 7.7 | 6.7 |
| 31.29 | 8.1 | 7.0 |
| 31.34 | 7.9 | 6.4 |
| 31.55 | 8.1 | 7.4 |
| 31.69 | 8.2 | 7.6 |
| 31.50 | 7.8 | 6.6 |
| 31.24 | 7.6 | 6.9 |
| 31.20 | 7.7 | 6.6 |
| 31.17 | 7.8 | 7.4 |
| 31.32 | 8.2 | 6.9 |
| 31.51 | 8.3 | 7.3 |
| 31.42 | 8.1 | 7.6 |
| 31.29 | 8.1 | 7.4 |
| 31.37 | 8.7 | 7.6 |
| 31.23 | 7.7 | 7.8 |
| 31.30 | 8.5 | 6.8 |
| 31.48 | 8.6 | 7.0 |
| 31.37 | 7.8 | 7.3 |
| Average thickness (mm) | 8.045 | 7.1 |

The thickness deviation between the measuring points (a) and (b) is 12%.

Inventive Example

Diapers Pampers Active Fit (Procter & Gamble, Germany) size 4 (maxi) where curly fiber and original ADL are replaced by ADL from Texsus, Italy (AB 2060BT, 60 g/m², Air through bonded).

TABLE 8

Thickness bi-folded inventive diaper

| Weight of diaper (g) | Thickness (a) (mm) | (b) (mm) |
|---|---|---|
| 27.20 | 4.7 | 4.4 |
| 27.29 | 4.9 | 4.3 |
| 27.12 | 4.7 | 3.6 |
| 27.34 | 5.0 | 4.7 |
| 27.29 | 4.8 | 4.1 |
| 27.33 | 4.6 | 3.7 |
| 27.42 | 4.9 | 5.1 |
| 27.46 | 5.0 | 5.2 |
| 27.39 | 4.7 | 4.9 |
| 27.42 | 5.3 | 4.3 |
| 27.49 | 4.6 | 5.4 |
| 27.40 | 4.7 | 5.4 |
| 27.23 | 4.6 | 4.6 |
| 27.39 | 5.3 | 4.6 |
| 27.27 | 4.9 | 5.2 |
| 27.40 | 4.6 | 4.6 |
| 27.36 | 4.9 | 4.1 |
| 27.45 | 4.6 | 5.8 |
| 27.38 | 4.7 | 4.4 |
| 27.48 | 4.8 | 5.4 |
| Average thickness (mm) | 4.815 | 4.69 |

The thickness deviation between the measuring points (a) and (b) is 3%.

The thickness deviation of the inventive diaper is significantly lower than the thickness deviation for the comparative diaper.

Unfolded Diaper

Thickness of the core of the unfolded diaper

Diapers Pampers Active Fit, size 4 (maxi) are used. The diapers are ripped of the curly fibers and the ADL are removed.

The measured thickness values of the core (with Poly-backsheet) for 20 cores are summarized in the following table.

TABLE 9

Results of the thickness measurements

| Diaper-core | Thickness at center (a) mm |
|---|---|
| 1 | 1.6 |
| 2 | 1.7 |
| 3 | 1.6 |
| 4 | 1.6 |
| 5 | 1.6 |
| 6 | 1.6 |
| 7 | 1.6 |
| 8 | 1.7 |
| 9 | 1.7 |
| 10 | 1.6 |
| 11 | 1.7 |
| 12 | 1.7 |
| 13 | 1.6 |
| 14 | 1.6 |
| 15 | 1.5 |
| 16 | 1.6 |
| 17 | 1.6 |
| 18 | 1.6 |
| 19 | 1.6 |
| 20 | 1.8 |
| Average thickness (mm) | 1.63 |

Thickness of the acquisition distribution layer Texsus (AB 2060BT, 60 g/m², Air Through Bonded)

The thickness of the ADL (acquisition distribution layer) Texsus (AB 2060BT, 60 g/m², Air Through Bonded) was measured analog to the procedure described for the unfolded diaper. The results (for 20 ADLs) are summarized in Table 10.

TABLE 10

Thickness of the ADL (Texsus)

| ADL (Texus) | Thickness at center (a) Mm |
|---|---|
| 1 | 0.70 |
| 2 | 0.71 |
| 3 | 0.80 |
| 4 | 0.78 |
| 5 | 0.80 |
| 6 | 0.80 |
| 7 | 0.85 |
| 8 | 0.82 |
| 9 | 0.93 |
| 10 | 0.80 |
| 11 | 0.82 |
| 12 | 0.82 |
| 13 | 0.90 |
| 14 | 0.83 |
| 15 | 0.83 |
| 16 | 0.83 |
| 17 | 0.79 |
| 18 | 0.84 |
| 19 | 0.80 |
| 20 | 0.86 |
| Average thickness (mm) | 0.82 |

The thickness of the ADL (Texsus) is almost 50% (0.82 mm) of the thickness of the core of the diaper (Pampers Active Fit, Maxi, 1.63 mm)

The invention claimed is:
1. A bi-folded diaper comprising
   a) an upper liquid-pervious layer,
   b) a lower liquid-impervious layer,
   c) a fluid-absorbent core between (A) and (B) comprising at least 90% by weight of fluid-absorbent polymer particles and not more than 10% by weight of cellulose based fibers, based on a sum of the fluid-absorbent polymer particles and the cellulose based fibers, and
   d) an acquisition-distribution layer between (A) and (C) comprising at least 90% by weight of synthetic non-cellulose based fibers and not more than 10% by weight of cellulose based fibers, based on a sum of the synthetic non-cellulose based fibers and the cellulose based fibers,
   wherein (i) the acquisition-distribution layer (D) is in longitudinal direction asymmetric positioned on the fluid-absorbent core (C) wherein a distance between the centers of the fluid-absorbent core (C) and the acquisition-distribution layer (D) is from 5 to 20% of a total length of the fluid-absorbent core in longitudinal direc- tion, (ii) a thickness of the acquisition-distribution layer (D) is not more than 60% of a thickness of the fluid-absorbent core (C), (iii) a thickness deviation of the bifolded diaper in longitudinal direction is less than 10%, (iv) and a thickness of an unfolded diaper is less than 3 mm, and wherein the diaper is bi-folded such that each longitudinal side is folded inward, then the diaper is folded once at the centre such that the diaper overlaps itself to form a rectangular shape.

2. The diaper according to claim 1, wherein the acquisition-distribution layer is essentially free of cellulose based fibers.

3. The diaper according to claim 1, wherein the fluid-absorbent core comprises less than 10% by weight of the cellulose based fibers.

4. The diaper according to claim 1, wherein the fluid-absorbent core comprises a hotmelt adhesive.

5. The diaper according to claim 1, herein the synthetic non-cellulose based fibers are based on polyester, polyethylene, polypropylene, polylactic acid, polyamide and/or blends thereof.

6. The diaper according to claim 1, wherein the fluid-absorbent core is encapsulated by wrapping with a nonwoven material or a tissue paper.

7. The diaper according to claim 1, wherein the fluid-absorbent polymer particles are placed in discrete regions of the fluid-absorbent core.

8. The diaper according to claim 1, wherein the fluid-absorbent core comprises at least 8 g of fluid-absorbent polymer particles.

9. The diaper according to claim 1 wherein the fluid-absorbent polymer particles have a bulk density of at least 0.55 g/cm$^3$.

10. The diaper according to claim 1, wherein the fluid-absorbent polymer particles have a centrifuge retention capacity of at least 24 g/g.

11. The diaper according to claim 1, wherein the fluid-absorbent polymer particles have absorbency under high load of at least 18 g/g.

12. The diaper according to claim 1, wherein the fluid-absorbent polymer particles have a saline flow conductivity of at least $20 \times 10^{-7}$ cm$^3$s/g.

13. A package comprising diapers according to claim 1.

14. The diaper according to claim 1 wherein the thickness of the unfolded diaper is 1.6 mm to less than 3 mm.

* * * * *